(12) United States Patent
Bjorklund et al.

(10) Patent No.: US 7,329,790 B2
(45) Date of Patent: Feb. 12, 2008

(54) WET SCRUBBING AND RECYCLE OF EFFLUENT-CONTAMINATING CATALYST PARTICLES IN AN OXYGENATE-TO-OLEFIN PROCESS

(75) Inventors: Bradford L. Bjorklund, Schaumburg, IL (US); John Q. Chen, Glenview, IL (US)

(73) Assignee: Uop LLC, Des Plaines, IL (US)

( * ) Notice: Subject to any disclaimer, the term of this patent is extended or adjusted under 35 U.S.C. 154(b) by 617 days.

(21) Appl. No.: 10/824,720

(22) Filed: Apr. 15, 2004

(65) Prior Publication Data

US 2005/0234281 A1    Oct. 20, 2005

(51) Int. Cl.
*C07C 7/00* (2006.01)
*C07C 1/00* (2006.01)

(52) U.S. Cl. .................. 585/640; 585/809; 585/638; 585/639

(58) Field of Classification Search ................ 585/640, 585/809, 638, 639
See application file for complete search history.

(56) References Cited

U.S. PATENT DOCUMENTS

| | | | |
|---|---|---|---|
| 4,387,263 A | 6/1983 | Vogt et al. | 585/640 |
| 4,440,871 A | 4/1984 | Lok et al. | 502/214 |
| 4,587,373 A | 5/1986 | Hsia | 585/639 |
| 4,873,390 A | 10/1989 | Lewis et al. | 585/638 |
| 5,095,163 A | 3/1992 | Barger | 585/640 |
| 5,126,308 A | 6/1992 | Barger et al. | 502/214 |
| 5,191,141 A | 3/1993 | Barger et al. | 585/640 |
| 5,744,680 A | 4/1998 | Mulvaney, III et al. | 585/640 |
| 6,121,504 A | 9/2000 | Kuechler et al. | 585/640 |
| 6,166,282 A | 12/2000 | Miller | 585/638 |
| 6,403,854 B1 | 6/2002 | Miller et al. | 585/638 |
| 7,119,241 B2 * | 10/2006 | Beech et al. | 585/640 |
| 7,135,604 B2 * | 11/2006 | Ding et al. | 585/809 |
| 2003/0088136 A1 | 5/2003 | Lumgair et al. | 585/640 |
| 2004/0064006 A1 | 4/2004 | Beech, Jr. et al. | 585/639 |
| 2004/0069684 A1 | 4/2004 | Tallman et al. | 208/161 |

* cited by examiner

*Primary Examiner*—Tam M. Nguyen
(74) *Attorney, Agent, or Firm*—Mark Goldberg

(57) ABSTRACT

The economics of a catalytic process using a fluidized conversion zone and a relatively expensive catalyst for converting an oxygenate to light olefins are substantially improved by recovering and recycling effluent contaminating catalyst particles from the product effluent stream withdrawn from the conversion zone which are present despite the use of one or more vapor-solid cyclone separating means to clean up this effluent stream. The contaminating catalyst particles are separated from this product effluent stream using a wet scrubbing zone and an optional dewatering zone to recover a slurry containing the contaminated particles which, quite surprisingly, can be successfully directly recycled to the oxygenate conversion zone or to the associated catalyst regeneration zone without loss of any substantial amount of catalytic activity thereby decreasing the amount of fresh catalyst addition required to make up for this source of catalyst loss.

22 Claims, 1 Drawing Sheet

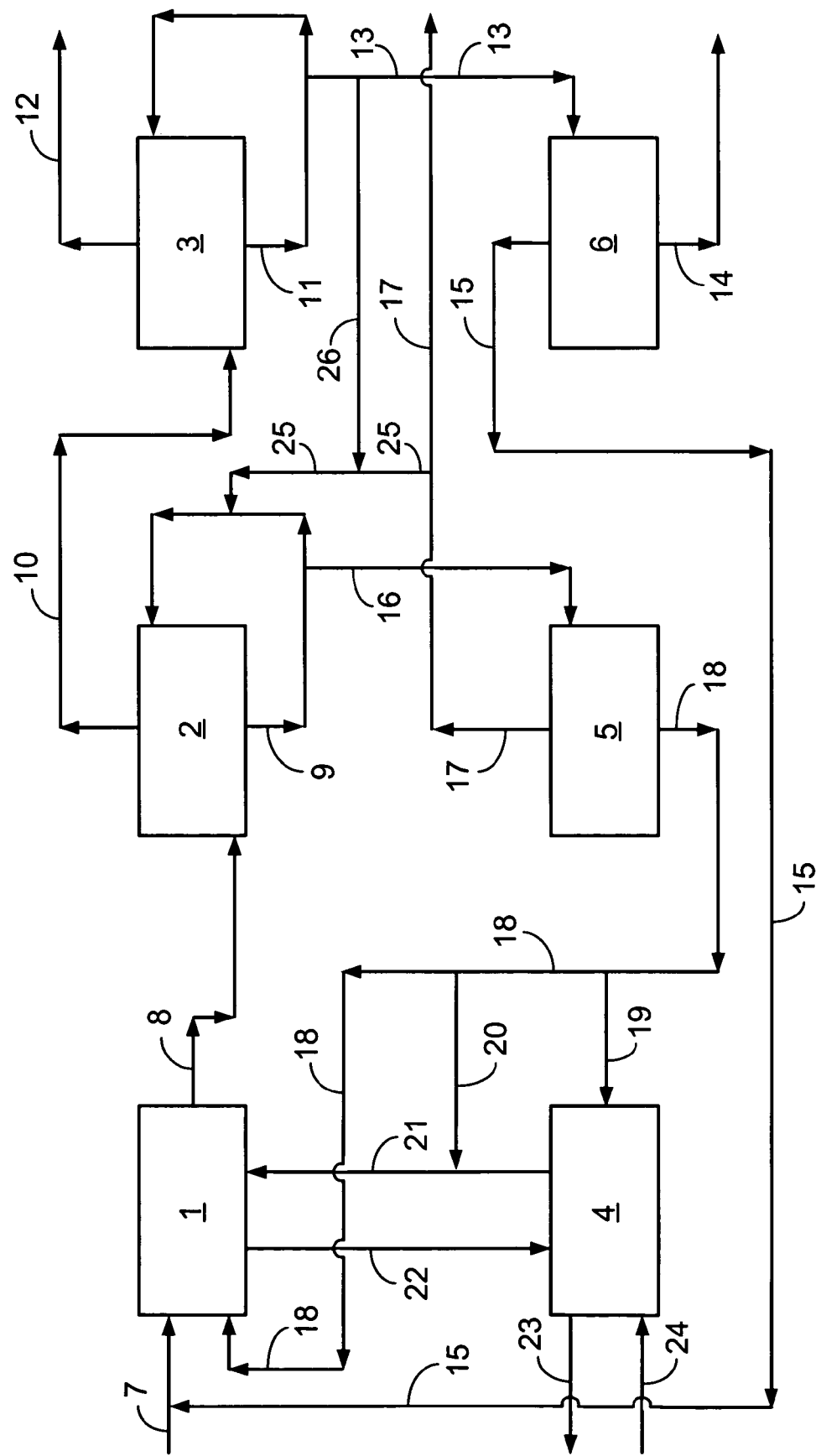

WET SCRUBBING AND RECYCLE OF EFFLUENT-CONTAMINATING CATALYST PARTICLES IN AN OXYGENATE-TO-OLEFIN PROCESS

FIELD OF INVENTION

The present invention relates generally to a method of catalyst conservation in an Oxygenate-To-Olefin (OTO) Process utilizing a fluidized oxygenate conversion zone and a relatively expensive catalyst containing an ELAPO molecular sieve wherein catalyst losses in the product effluent stream withdrawn from the fluidized oxygenate conversion zone are significantly reduced by the use of a wet scrubbing step on this product effluent stream in order to recover a slurry of these contaminating catalyst particles in a scrubbing liquid which quite surprisingly can be directly recycled either to the oxygenate conversion zone or to the associated catalyst regeneration zone with no significant reduction in the catalytic activity of these recovered catalyst particles. The present invention more specifically relates to a method of improving the overall economics of an OTO process that utilizes a fluidized conversion zone in combination with a relatively expensive catalyst containing an ELAPO molecular sieve wherein the product effluent stream withdrawn from the oxygenate conversion zone is contaminated with catalyst particles despite the use of one or more vapor-solid separation means to clean up this product effluent stream and wherein the loss of these catalyst particles in this effluent stream requires a significant expense for additional fresh catalyst in order to replace the catalyst lost in the product effluent stream. The solution to this catalyst loss problem is provided by the present invention and involves the use of a wet scrubbing step on this product effluent stream in order to recover a slurry containing the contaminating catalyst particles with subsequent recycle of at least a portion of this slurry either to the oxygenate conversion zone or to the associated catalyst regeneration zone, thereby greatly diminishing the amount of fresh catalyst that must be provided in order to cover this source of catalyst loss. The key to the instant invention essentially involves recognition that these effluent-contaminating catalyst particles containing an ELAPO molecular sieve have been coated with a protective layer of carbonaceous deposits (commonly called coke) during their passage through the conversion zone and this protective layer of coke prevents the loss of any significant amount of catalytic activity when these catalyst particles are recovered in a wet scrubbing step and a slurry containing these recovered particles is returned directly to the oxygenate conversion step or to the associated deactivated catalyst regeneration step.

The present invention relates even more specifically to a method of catalyst conservation in a Methanol-To-Olefin (MTO) process that utilizes a fluidized catalytic conversion zone and a relatively expensive catalyst containing a SAPO molecular sieve wherein despite the use of one or more vapor-solid separating means to remove catalyst particles from the vaporous product effluent stream there is still a significant amount of these particles contaminating this stream and wherein these particles are recovered from this product effluent stream utilizing a wet scrubbing step operated with an aqueous scrubbing liquid under conditions to remove substantially all of these contaminating particles from the product effluent stream with subsequent recycling of at least a portion of the recovered catalyst particles either directly to the fluidized MTO conversion zone or to the associated deactivated catalyst regeneration step, thereby significantly diminishing the amount of fresh catalyst that must be added to the MTO conversion zone to make-up for this source of catalyst losses.

BACKGROUND OF INVENTION

A major portion of the worldwide petrochemical industry is concerned with the production of light olefin materials and their subsequent use in the production of numerous important chemical products via polymerization, oligomerization, alkylation and the like well-known chemical reactions. Light olefins include ethylene, propylene and mixtures thereof. These light olefins are essential building blocks for the modern petrochemical and chemical industries. The major source for these materials in present day refining is the steam cracking of petroleum feeds. For various reasons including geographical, economic, political and diminished supply considerations, the art has long sought a source other than petroleum for the massive quantities of raw materials that are needed to supply the demand for these light olefin materials. In other words, the holy grail of the R & D personnel assigned to work in this area is to find a way to effectively and selectively use alternative feedstocks for this light olefin production application thereby lessening dependence of the petrochemical industry on petroleum feedstocks. A great deal of the prior art's attention has been focused on the possibility of using hydrocarbon oxygenates and more specifically methanol as a prime source of the necessary alternative feedstock. Oxygenates are particularly attractive because they can be produced from such widely available materials as coal, natural gas, recycled plastics, various carbon waste streams from industry and various products and by-products from the agricultural industry. The art of making methanol and other oxygenates from these types of raw materials is well established and typically involves the use of one or more of the following procedures: (1) manufacture of synthesis gas by any of the known techniques typically using a nickel or cobalt catalyst followed by the well-known methanol synthesis step using relatively high pressure with a copper-based catalyst; (2) selective fermentation of various organic agricultural products and by-products in order to produce oxygenates; or (3) various combinations of these techniques.

Given the established and well-known technologies for producing oxygenates from alternative non-petroleum raw materials, the art has focused on different procedures for catalytically converting oxygenates such as methanol into the desired light olefin products. These light olefin products that are produced from non-petroleum based raw materials must of course be available in quantities and purities such that they are interchangeable in downstream processing with the materials that are presently produced using petroleum sources. Although many oxygenates have been discussed in the prior art, the principal focus of the two major routes to produce these desired light olefins has been on methanol conversion technology primarily because of the availability of commercially proven methanol synthesis technology. A review of the prior art has revealed essentially two major techniques that are discussed for conversion of methanol to light olefins. The first of these MTO processes is based on early German and American work with a catalytic conversion zone containing a zeolitic type of catalyst system. Representative of the early German work is U.S. Pat. No. 4,387,263 which was filed in May of 1982 in the U.S. without a claim for German priority. This '263 patent reports on a series of experiments with methanol conversion techniques using a ZSM-5-type of catalyst system wherein the problem of DME recycle is a major focus of the technology disclosed. Although good yields of ethylene and propylene were reported in this '263 patent, they unfortunately were accompanied by substantial formation of higher aliphatic and aromatic hydrocarbons which the patentees speculated might be useful as an engine fuel and specifically as a gasoline-type of material. In order to limit the amount of this heavier material that is produced, the patentees of the '263 patent propose to limit conversion to less than 80% of the methanol charged to the MTO conversion step. This operation at lower conversion levels necessitated a critical assessment of means for recovering and recycling not only unreacted methanol but also substantial amounts of a DME intermediate product. The focus then of the '263 patent invention was therefore on a DME and methanol scrubbing step utilizing a water solvent in order to efficiently and effectively recapture the light olefin value of the unreacted methanol and of the intermediate reactant DME.

This early MTO work with a zeolitic catalyst system was then followed up by the Mobil Oil Company who also investigated the use of a zeolitic catalyst system like ZSM-5 for purposes of making light olefins. U.S. 4,587,373 is representative of Mobil's early work and it acknowledged and distinguished the German contribution to this zeolitic catalyst based MTO route to light olefins. The inventor of the '373 patent made two significant contributions to this zeolitic MTO route the first of which involved recognition that a commercial plant would have to operate at pressure substantially above the preferred range that the German workers in this field had suggested in order to make the commercial equipment of reasonable size when commercial mass flow rates are desired. The '373 patent recognized that as you move to higher pressure for the zeolitic MTO route in order to control the size of the equipment needed for commercial plant there is a substantial additional loss of DME that was not considered in the German work. This additional loss is caused by dissolution of substantial quantities of DME in the heavy hydrocarbon oil by-product recovered from the liquid hydrocarbon stream withdrawn from the primary separator. The other significant contribution of the '373 patent is manifest from inspection of the flow scheme presented in FIG. 2 which prominently features a portion of the methanol feed being diverted to the DME absorption zone in order to take advantage of the fact that there exist a high affinity between methanol and DME thereby downsizing the size of the scrubbing zone required relative to the scrubbing zone utilizing plain water that was suggested by the earlier German work.

Primarily because of an inability of this zeolitic MTO route to control the amounts of undesired $C_4^+$ hydrocarbon products produced by the ZSM-5 type of catalyst system, the art soon developed a second MTO conversion technology based on the use of a non-zeolitic molecular sieve catalytic material. This branch of the MTO art is perhaps best illustrated by reference to UOP's extensive work in this area as reported in numerous patents of which U.S. Pat. No. 5,095,163, U.S. Pat. No. 5,126,308 and U.S. Pat. No. 5,191,141 are representative. This second approach to MTO conversion technology was primarily based on using a catalyst system comprising a non-zeolitic molecular sieve, generally a metal aluminophosphate (ELAPO) and more specifically a silicoaluminophosphate molecular sieve (SAPO), with a strong preference for a SAPO species that is known as SAPO-34. This SAPO-34 material was found to have a very high selectivity for light olefins with a methanol feedstock and consequently very low selectivity for the undesired corresponding light paraffins and the heavier materials. This ELAPO catalyzed MTO approach is known to have at least the following advantages relative to the zeolitic catalyst route to light olefins: (1) greater yields of light olefins at equal quantities of methanol converted; (2) capability of direct recovery of polymer grade ethylene and propylene without the necessity of the use of extraordinary physical separation steps to separate ethylene and propylene from their corresponding paraffin analogs; (3) sharply limited production of by-products such as stabilized gasoline; (4) flexibility to adjust the product ethylene-to-propylene weight ratios over the range of 1.5:1 to 0.75:1 by minimal adjustment of the MTO conversion conditions; and (5) significantly less coke make in the MTO conversion zone relative to that experienced with the zeolitic catalyst system.

For various reasons well articulated in UOP's patents, U.S. Pat. No. 6,403,854, U.S. Pat. No. 6,166,282 and U.S. Pat. No. 5,744,680 (all of the teaching of which are hereby specifically incorporated by reference) the consensus of the practitioners in this OTO or MTO art points to the use of a fluidized reaction zone along with our associated fluidized regeneration zone as the preferred commercial solution to the problem of effectively and efficiently using an ELAPO or SAPO-type of catalyst system in this type of service. As is well-understood by those of skill in the fluidization art, the use of this technology gives rise to a substantial problem of solid-vapor separation in order to efficiently separate the particles of the fluidized catalyst from the vapor products of the OTO or MTO reaction as well as from any unreacted oxygenate materials exiting the OTO or MTO conversion zone. Standard industry practice for accomplishing this difficult separation step involves its use of one or more vapor-solid cyclonic separating means which are well illustrated in the sole drawing of U.S. Pat. No. 6,166,282 where a series of three cyclonic separation means are used to separate spent OTO or MTO catalyst from the product effluent stream. As is clear from the teachings of these three UOP patents as well as the teachings of U.S. Pat. No. 6,121,504 and US-A-2003/0088136 these still remain a very substantial problem of OTO or MTO catalyst contamination of the product effluent stream withdrawn from the fluidized conversion zone.

Despite the promising developments associated with the ELAPO or SAPO catalyzed routes to light olefins there are still substantial hurdles to overcome before an economically attractive OTO or MTO process can be fully realized. One very substantial economic problem is associated with the amount of fresh catalyst that must be added to the OTO or fluidized conversion zone in order to maintain the catalyst inventory in the OTO conversion system at design levels when the product effluent stream from the OTO conversion zone contains substantial amounts of contaminating catalyst particles which in the processes of the prior art discussed above are not recovered and recycled to the OTO conversion zone. This problem of effluent contamination by catalyst particles is made more significant in the non-zeolitic catalyzed route to the desired light olefins because of the relatively expensive nature of the ELAPO or SAPO molecular sieves used therein compared to the corresponding zeolitic molecular sieve, ZSM-5, which has been used and exemplified in many of the prior art OTO conversion processes. Current economic conditions are such that the cost of an equivalent amount of an ELAPO-containing catalyst system is expected to differ from the cost of the prior art zeolitic system by a factor of about 5 to 40 even considering the expected substantial savings in costs that will be associated with the large scale production of ELAPO molecular sieve for this particular application. The problem addressed by the present invention is then to provide a method for recovery and recycle of these effluent-contaminating catalyst particles that are present in the product effluent stream withdrawn from an OTO conversion zone that utilizes a fluidized transport bed system in combination with a relatively expensive ELAPO molecular sieve-containing catalyst system. In other words, the problem addressed by the present invention is to staunch the loss of catalyst particles from a fluidized OTO conversion zone operated with a relatively expensive catalyst system containing an ELAPO molecular sieve in order to decrease the consumption of the relatively expensive catalyst system and thereby improve the economics of the resulting OTO or MTO conversion process.

The solution envisioned and provided by the present invention to this catalyst loss problem involves the use of a wet scrubbing step designed to recover substantially all of the product effluent contaminating catalyst particles and to provide a slurry of these catalyst particles in a scrubbing liquid such as water with subsequent recycle of at least a portion of the catalyst particles contained in the resulting slurry to the OTO conversion zone or to the associated deactivated OTO catalyst regeneration zone thereby recapturing the catalytic activity of these contaminating catalyst particles and diminishing the need for fresh catalyst that must be added to the system in order to make-up for this source of catalyst losses. The key developments that enable the instant invention are our findings that the catalytic activity of these effluent-contaminating catalyst particles will survive not only the hydrothermal shock associated with the introduction of these relatively hot particles contained in this product effluent stream into a relatively cool wet scrubbing zone which captures these particles by immersion in a scrubbing liquid which is typically aqueous but also the direct return of these particles, after an optional concentration step, to either the relatively hot OTO conversion zone or to the relatively hot spent OTO catalyst regeneration zone without any additional treatment. The fact that the catalytic activity of these recaptured catalyst particles will survive the hydrothermal shocks associated with introduction into the wet scrubbing zone as well as the thermal shocks associated with return to either the OTO conversion zone or the associated catalyst regeneration zone are quite surprising in view of the substantial prejudice in the prior art to exposure of ELAPO-containing molecular sieve to immersion in a liquid such as water. For example, U.S. Pat. No. 5,744,680 discloses the use of a wet scrubbing step on the cooled effluent stream from an OTO conversion zone in order to remove ELAPO molecular sieve-containing catalyst particles from this effluent stream and prepare this effluent stream for downstream compression. However, the '680 patent merely teaches at column 8, lines 38 to 48 that the catalyst-containing bottom stream from the wet scrubbing step is withdrawn via line 28 from scrubbing zone 104 for further treatment which is unspecified. There is no teaching indicating that the activity value of these catalyst particles recovered from this wet scrubbing step can be recaptured for use in the OTO conversion zone. With reference to the drawing of the '680 patent the wet scrubbing zone is shown as zone 104 with injection of a scrubbing fluid comprising $H_2O$ via line 24 and recovery of a bottom slurry material containing a mixture of catalyst finds and water via line 2. Further evidence of the art's failure to recognize that the catalytic activity of these effluent-contaminating catalyst particles can be recaptured and reused is shown in U.S. Pat. No. 6,121,504 wherein a wet scrubbing is used for the purposes of quenching the effluent stream from the OTO conversion zone to produce a bottom stream which is cooled and recirculated to the wet scrubbing stream with a drag stream withdrawn from the recirculating scrubbing fluid and charged to a stripping zone for purposes of heat recovery. With reference to the drawing of the '504 patent the scrubbing quench zone is zone 13 and the catalyst-containing bottom stream is represented by line 15 with the drag stream being taken from line 17 after pump 16 is used to change the pressure of this circulating scrubbing liquid. A careful reading of the teachings of the '504 patent has failed to reveal any discussion of the presence or disposition of catalyst particles that are inherently entrained in the bottom stream from zone 13 when the OTO conversion zone 10 is operated in a fluidized mode. The sole example of the '504 patent exemplifies a fluidized OTO conversion operation without any discussion of the fate of the catalyst particles that are inherently entrained in the product effluent stream recovered therefrom. In a subsequent published application US2003/0088136A1 emanating from the same ExxonMobil Chemical Company responsible for the '504 patent, the teachings of the '504 patent are characterized and distinguished in paragraph 0007 by pointing out that the '504 patent "provides no guidance on how to manage the catalyst particles that exit the reactor entrained with the gaseous effluent stream." Additional evidence that the prior art failed to recognize that the catalyst particles recovered from the product effluent stream of OTO process could be recovered by wet scrubbing and recycled to the OTO conversion zone without loss of their catalytic activity is shown in U.S. Pat. No. 6,403,854 wherein FIG. 2 exemplifies a two-stage quench arrangement for the hot effluent stream recovered from the OTO conversion zone and wherein in fact the first stage is a wet scrubbing zone employed for the purposes of neutralizing acidic materials that are by-product of the OTO conversion reaction and of removing catalyst fines entrained in the product effluent stream. The teachings of the '854 patent on this subject are concisely set forth in the first full paragraph of column 10 wherein the operation of wet scrubbing zone 42 (called therein first stage quench tower) is described. The scrubbing liquid is introduced into column 42 via line 24 and the resulting bottom stream is divided and a portion is used as a pump-around stream via lines 23 and 24 to act as the scrubbing liquid utilized in zone 42 with a drag stream withdrawn via lines 23 and 25 and this drag stream comprising the majority of the impurities and catalyst fines is concentrated into a small stream which is taught as comprising about 5 to about 10 wt-% of the total recovered water. Careful reading of the '854 patent has failed to reveal any hint or suggestion of possible recovery and reuse of the catalyst particles that are contained in the drag stream from the first stage of the two-stage quench zone exemplified therein. Additional convincing evidence of the prejudice in the prior art against recovery and reuse of the effluent contaminating catalyst particles is evident from a reading of the previously mentioned application publication from ExxonMobil Chemical Company, US2003/0088136A1, which was relatively recently published (i.e. May 8, 2003) and fully discloses the problem of product effluent contamination with catalyst particles in a section starting with paragraph 0037 and running through paragraph 0047 wherein the contamination of this product effluent stream is described and quantified. The use of a wet scrubbing zone in order to remove these contaminating particles is described in the '136 application on page 7 beginning at paragraph 0064 running through paragraph 0070. In the last sentence of 0070 applicants teach that the quench device serves two purposes in a single unit "that of washing to separate entrained solids in a dilute liquid stream and condensing components of the effluent stream, for example water, which in certain applications is beneficial to further processing in the recovery train." The '136 published application does not however provide for any means of recovery and reuse of the catalyst particles that are concentrated in the bottom stream from the dual purpose quench zone described therein. This is particularly clear in the teachings of the sole example of the '136 published application which is contained in paragraph 0082.

The problem solved by the present invention is then in a nutshell to remedy the prejudices of the prior art and provide an OTO conversion process that utilizes a fluidized bed reactor system in combination with relatively expensive ELAPO-containing catalyst particles to enable not only the successful recovery of these product effluent-contaminating catalyst particles but also their reuse in the OTO catalytic conversion zone in order to recapture their catalytic activity. The invention thus substantially improve the economics of the overall process by diminishing the need for fresh catalyst make-up to compensate for this source of catalyst loss.

SUMMARY OF THE INVENTION

The primary objective to the present invention is to provide a realistic and technically feasible solution to the problem of catalyst loss in the product effluent from an OTO or MTO reaction zone utilizing a fluidized reactor system and a relatively expensive ELAPO catalyst system. A secondary objective is to improve the economics of an OTO process that utilizes a fluidized reaction zone in combination with a relatively expensive catalyst system containing an ELAPO molecular sieve wherein the improvement is associated with a diminished requirement for make-up fresh catalyst due to the present invention's capability of staunching the loss of the catalyst in the product effluent stream recovered from the OTO conversion zone. A more general object is to provide a flow scheme for use in a OTO conversion process which enables the recovery and recycle of product effluent contaminating catalyst particles that in the prior art represented a substantial and continuing loss of catalyst from the OTO process that significantly contribute to the demand for fresh catalyst make-up in order to maintain the circulating inventory of catalyst in the OTO reactor/regenerator system.

We have now found a solution to this problem of loss of expensive ELAPO-containing catalyst particles in the product effluent stream withdrawn from the fluidized OTO conversion zone and our solution essentially involves the use of a wet scrubbing step, designed to wash the contaminating catalyst particles from this effluent stream and to produce a relatively catalyst-free vaporous overhead stream containing the light olefin products and other materials as well as a bottom stream containing a slurry of the contaminating catalyst particles in a scrubbing liquid, in combination with a direct recycle step in which at least a portion of the resulting catalyst slurry is passed either to the OTO conversion zone or to the associated regeneration zone, thereby recapturing the activity of these contaminating catalyst particles. An associated finding is that an ELAPO-molecular sieve-containing catalyst system tolerates the hydrothermal shock associated with the wet scrubbing step which is typically run at a temperature considerably lower then the temperature of the entering effluent stream and also the thermal shock associated with recycling at least a portion of the relatively cool slurry of catalyst particles back to the hot OTO conversion zone or the hot catalyst regeneration zone. A key enabling finding here is that the activity of an ELAPO molecular sieve-containing particles survives immersion in a scrubbing liquid provided that the particles are covered with a protective layer of carbonaceous deposits accumulated during the passage of these fluidized particles through the OTO conversion zone.

Without the intention of being limited by this explanation, we believe that the carbonaceous deposits or coke that is deposited on the catalyst particles in the OTO conversion zone acts to insulate the ELAPO molecular sieve from the adverse effects of immersion in a scrubbing liquid that is typically aqueous in nature. The beneficial nature of these carbonaceous deposits will be highlighted in a comparative example presented hereinafter by comparison of the effect of immersion in an aqueous scrubbing liquid of an ELAPO-containing OTO catalyst with and without these carbonaceous deposits. Despite the significant body of art cited above that teaches the use of a wet scrubbing step to remove these contaminating catalyst particles from the effluent stream from a fluidized OTO process, we believe that we are the first to recognize that the recovered particles still retain significant catalytic activity and they can be directly recycled back to the OTO reactor/regenerator system where the carbonaceous deposits can be removed and the resulting revitalized catalyst particles can then be used to catalyze further the OTO reaction sequence.

In one embodiment consequently the instant invention is a process for the catalytic conversion of the feedstream containing an oxygenate to light olefins which uses a fluidized conversion zone and a relatively expensive fluidized catalyst containing an ELAPO molecular sieve with recovery and recycle of contaminating catalyst particles from the product effluent stream withdrawn from the fluidized conversion zone. In the first step of the process the feedstream is contacted with the fluidized catalyst in the fluidized conversion zone at conversion conditions effective to form a mixture of the activated catalyst particles and olefinic reaction products. In the second step at least a portion of the deactivated catalyst particles is separated from the resulting mixture in a vapor-solid separating zone containing one or more vapor-solid cyclonic separating means operated at separating conditions effective to form a stream of deactivated catalyst particles and a conversion zone product effluent stream containing light olefins, unreacted oxygenates, $H_2O$, other reaction products and undesired amounts of contaminating catalyst particles. In the third step the resulting product effluent stream is passed to a wet scrubbing zone and therein contacted with a scrubbing liquid under scrubbing conditions effective to form a substantially catalyst-free vaporous overhead stream containing light olefins, unreacted oxygenates, olefinic by-products and water and a liquid bottom stream containing a mixture of the contaminating catalyst particles and the scrubbing liquid. In the fourth step at least a portion of the stream of deactivated catalyst particles separated in the second step is passed to a regeneration zone and therein contacted with an oxidizing gas stream under oxidizing conditions effective to form a stream of regenerated catalyst particles. In the next step at least a portion of the liquid bottom stream produced in the wet scrubbing zone is recycled either to the OTO conversion step or the catalyst regeneration step. In the last step then the stream of freshly regenerated catalyst particles recovered from the regeneration step is recycled to the OTO conversion zone.

The second embodiment involves the OTO conversion process that is described in the first embodiment wherein at least a portion of the liquid bottom stream recovered from the wet scrubbing zone is passed to a liquid-solid separating zone containing one or more liquid-solid separating means operated under separating conditions effective to produce a solid-rich stream containing a relatively rich slurry of contaminated catalyst in the scrubbing liquid and a relatively solid-lean stream containing scrubbing liquid. At least a portion of the solid-rich stream is then recycled to the OTO conversion step or to the deactivated catalyst regeneration step in order to recapture the activity value of the contaminating particles.

A highly preferred embodiment of the present invention comprises an OTO conversion process as described above in the first embodiment wherein the oxygenate present in the feedstream is methanol or dimethylether or a mixture thereof and wherein the ELAPO molecular sieve is a SAPO molecular sieve having its crystal structure corresponding to SAPO-34 or SAPO-17 and wherein the scrubbing liquid used in the wet scrubbing zone is water optionally containing an alkaline reagent compatible with SAPO-34 and SAPO-17 in an amount sufficient to neutralize a significant portion of any acidic by-products of the oxygenate conversion reaction that are present in the product effluent stream withdrawn from the OTO conversion zone.

A heat integrated embodiment of the present invention involves the process as described above in the first embodiment wherein the conversion zone product effluent stream which is at a temperature of about 350° to about 600° C. upon exit from the MTO conversion zone is substantially cooled between the conversion step and the wet scrubbing step by use of steam generation and/or by indirect heat exchange against the oxygenate feedstream in order to recapture at least a portion of the exothermic heated reaction liberated in the OTO conversion zone by using it to preheat and vaporize at least a portion of the feedstream charged to the OTO process.

Other objects, embodiments, advantages and features of the present invention will be clear to someone of ordinary skill in the chemical engineering art from a detailed examination of the following description of the invention as well as the attached drawing.

BRIEF DESCRIPTION OF THE DRAWING

The FIGURE is a process flow diagram of a preferred integrated embodiment of the present invention which portrays the essential interconnections, interactions and interrelationships between the various operating zones preferably utilized to recover and directly recycle the contaminating catalyst particles that are present in the product effluent stream withdrawn from the OTO conversion zone.

TERMS AND CONDITIONS DEFINITIONS

The following terms and conditions are used in the present specification with the following meanings: (1) a "portion" of a stream means either an aliquot part that has the same composition as the whole stream or a part that is obtained by eliminating a readily separable component therefrom (e.g. if the stream contains hydrocarbons in admixture with steam, then after condensation of a major portion of the steam, it comprises an aqueous portion and a hydrocarbon portion). (2) an "overhead" stream means the net overhead recovered from the specified zone after recycle of any portion to the zone for reflux or any other reason. (3) a "bottom" stream means the net bottom stream from the specified zone obtained after recycle of any portion for purposes of reheating and/or reboiling and/or after any phase separation. (4) a line is "blocked-off" when it contains a valve that is set to a position that prevents flow through the line. (5) presence of necessary compressors and/or pumps is understood when flow is shown from a zone of relatively low pressure to a zone of higher pressure. (6) presence of necessary heating and/or cooling means is implied when flow is shown between zones operating at different temperatures. (7) an ingredient is "lifted" or "stripped" when it is concentrated in the overhead stream withdrawn from the specified zone. (8) a "vapor" stream means a stream containing one or more components in the gaseous state. (9) the term "light olefins" means ethylene, propylene and mixtures thereof. (10) The expression "ELAPO" molecular sieve means a material having a three-dimensional microporous framework structure of $ALO_2$, $PO_2$ and $ELO_2$ tetrahedral units having the empirical formula:

where EL is a metal selected from the group consisting of silicon, magnesium, zinc, iron, cobalt, nickel, manganese, chromium and mixtures thereof, x is the mole fraction of EL and is at least 0.005, y is the mole fraction of Al and is at least 0.01 z is the mole fraction of P and is at least 0.01 and x+y+z=1. When EL is a mixture of metals, x represents the total amount of the metal mixture present. Preferred metals (EL) are silicon, magnesium and cobalt with silicon being especially preferred. (11) The expression "SAPO molecular sieve" means an ELAPO molecular sieve wherein the EL element is silicon as described in U.S. Pat. No. 4,440,871. (12) The expression "OTO" process means a process for converting an oxygenate to light olefins and in a preferred embodiment when the oxygenate is methanol the OTO process is referred to as an MTO process herein. (13) The term "oxygenate" means an oxygen-substituted aliphatic hydrocarbon preferably containing 1 to 4 carbon atoms. (14) A reagent is "compatible" with a catalyst system when the physical, chemical and catalytic properties of the catalyst are not permanently altered by interaction with the reagent.

DETAILED DESCRIPTION OF THE INVENTION

In the instant OTO process the feedstream comprises one or more oxygenates. The term "oxygenate" is employed herein to include alcohols, ethers, and carbonyl compounds (e.g. aldehydes, ketones, carboxylic acids, and the like). The oxygenate feedstock preferably contains at least one oxygen atom and about 1 to 10 carbon atoms and, and preferably, contains from about 1 to 4 carbon atoms. Suitable oxygenates include lower straight or branched chain alkanols, and their unsaturated counterparts. Representatives of suitable oxygenate compounds include methanol, dimethyl ether (DME), ethanol, diethyl ether, methylether, formaldehyde, dimethyl ketone, acetic acid, and mixtures thereof.

In the OTO conversion step of the present invention, the oxygenate feedstock is catalytically converted to hydrocarbons containing aliphatic moieties such as—but not limited to—methane, ethane, ethylene, propane, propylene, butylene, and limited amounts of other higher aliphatics by contacting the feedstock with a an ELAPO-containing catalyst. A diluent is not required but is a useful option to maintain the selectivity of the catalyst to produce light olefins, particularly ethylene and propylene. The use of a diluent such as steam can provide certain equipment cost and thermal efficiency advantages as well as lowering the partial pressure of the oxygenate reactants, thereby increasing selectivity to olefins. The phase change between steam and liquid water can also be employed to advantage in transferring heat between the feedstock and the reactor effluent, and the separation of the steam diluent from the product requires simple condensation of the water to separate the water from the hydrocarbons. Ratios of 1 mole of oxygenates to about 0.1-5 moles of diluent have been disclosed as being useful in the OTO conversion reaction. The preferred diluent is steam.

The oxygenate conversion step of the present invention is preferably conducted such that the oxygenate feedstock is contacted in a vapor phase in a reaction zone with a ELAPO molecular sieve catalyst at effective conversion conditions to produce olefinic hydrocarbons, i.e., an effective temperature, pressure, weight hourly space velocity (WHSV) and, optionally, an effective amount of diluent. The OTO step is affected for a period of time sufficient to produce the desired light olefin products. The oxygenate conversion step is effectively carried out over a wide range of pressures, including autogenous pressures. At pressures between about 0.1 atmospheres (10.1 kPa) and about 100 atmospheres (10.1 MPa), the formation of light olefin products will be affected although the optimum amount of product will not necessarily form at all pressures. The preferred pressure is between about 0.5 atmospheres (50.6 kPa) and about 20 atmospheres (2.0 MPa). The pressure will more preferably range from about 1 to about 10 atmospheres (101.3 to 1013.3 kPa). The pressures referred to herein are exclusive of any diluent and refer to the partial pressure of the oxygenate feedstock. The temperature which may be employed in the oxygenate conversion step may vary over a wide range depending, at least in part, on the selected ELAPO molecular sieve catalyst. In general, the OTO step can be conducted at an effective temperature between about 350° and about 600° C.

In the oxygenate conversion step of the present invention, it is preferred that the ELAPO catalysts have relatively small pores. Preferably, the small pore catalysts have a substantially uniform pore structure, e.g., substantially uniformly sized and shaped pore with an effective diameter of less than about 5 Angstroms. Suitable catalyst may comprise an ELAPO molecular sieve and a matrix material. A preferred ELAPO molecular sieve is one in which the element (EL) content varies from about 0.005 to about 0.2 mole fraction and in which EL is silicon (usually referred to as SAPO). The SAPOs which can be used in the instant invention are preferably any of those described in U.S. 4,440,871; U.S. 5,126,308, and U.S. 5,191,141 (all of which are hereby specifically incorporated by reference). Especially preferred SAPOs include the SAPO-34 and SAPO-17 structures with SAPO-34 being most preferred.

The ELAPO catalyst is preferably incorporated into solid particles containing one or more matrix materials in which the catalyst is present in an amount effective to promote the desired oxygenate conversion reactions. In one aspect, the solid particles comprise a catalytically effective amount of the catalyst and at least one matrix material, preferably selected from the group consisting of binder materials, filler materials, and mixtures thereof in an amount selected to provide desired properties, e.g., desired catalyst dilution, mechanical strength, and the like to the solid particles. Such matrix materials are preferably porous in nature and may contribute to or promote one or more of the desired oxygenate conversion reactions-particularly the conversion of methanol to DME. Filler and binder materials include, for example, synthetic and naturally occurring substances such as metal oxides, clays, silicas, aluminas, silica-aluminas, silica-magnesias, silica-zirconias, silica-thorias, silica-berylias, silica-titanias, silica-alumina-thorias, silica-alumina-zirconias, alumino-phosphates, mixtures of these and the like. If matrix materials, e.g., binder and/or filler materials, are included in the catalyst composition, the molecular sieves preferably comprise about 1 to about 99 percent, more preferably about 5 to about 90 percent and still more preferably about 5 to about 60 percent, by mass of the total composition. The preparation of solid particles comprising ELAPO catalyst and matrix materials in a fluidized size range is conventional and well known in the spray drying art and, therefore, need not be discussed in detail herein.

During the oxygenate conversion reactions, a carbonaceous material, i.e., coke, is deposited on the catalyst in an amount of about 1 to 20 mass-% and more commonly about 1.5 to 9 mass-%. The carbonaceous deposit material has the effect of reducing the number of available active sites on the catalyst which thereby affects the extent of the conversion. During the OTO conversion step a portion of the coked catalyst is withdrawn from the OTO reaction zone and passed to a regeneration step where it is regenerated with an oxygen-containing medium (e.g. air) to remove at least a portion of the carbonaceous material and returned to the oxygenate conversion reaction zone. Depending upon the particular catalyst and conversion, it may be desirable to substantially remove the carbonaceous material e.g., to less than 0.5 mass-%, or only partially regenerate the catalyst, e.g., to from about 1 to 3 mass-% carbonaceous material. Preferably, the regenerated catalyst will contain about 0 to about 3 mass-% and more preferably from about 0 to about 1 mass-% carbonaceous material (i.e. coke). During regeneration there can be additional oxidation of sulfur and in some instances nitrogen compounds along with the removal of any contaminant metal materials from the catalyst. Regeneration conditions can be varied moreover depending upon the type of ELAPO catalyst used and the type of contaminant material present upon the catalyst prior to its regeneration. See U.S. Pat. No. 4,873,390 for additional information on oxidation regeneration techniques for ELAPO catalysts.

The problem of recovery of ELAPO catalyst particles from the product effluent stream withdrawn from the OTO conversion zone is a problem that is unique to a fluidized bed type of system. In a fluidized system large amounts of finely divided catalyst particles are continuously transported between a reaction zone and a regeneration zone and in the OTO reaction zone they are admixed with the oxygenate feedstream in an amount which is conveniently measured in terms of a WHSV calculated on the basis of mass hourly flow rate of the sum of the mass of oxygenate reactants passed to the MTO conversion zone plus any other oxygenate or hydrocarbon reactants present in the feed or recycle streams divided by the mass of the ELAPO catalyst present in the OTO conversion zone. WHSV for use in the fluidized in the OTO conversion zone associated with the present invention can range from about 0.1 to about 100 $hr^{-1}$ with best results obtained within the range of about 0.5 to 40 $hr^{-1}$. Since the OTO conversion reactions are strongly exothermic a significant temperature increase will occur across the OTO reaction zone which is ordinarily of the magnitude of about 100° to 400° C. (180° to 720° F.) and thus unlike traditional hydrocarbon FCC practice, the catalyst circulation rate is not set on the basis of the amount required to provide sufficient heat to the endothermic reactions that are traditionally involved in hydrocarbon FCC practice. In a fluidized OTO reactor system, the catalyst circulation rate between the reactor and the regenerator will ordinarily be set at a minimum level designed to hold average coke on the circulating catalyst inventory of the ELAPO catalyst entering the conversion step in the range of about 1 to 20 mass-% of the active ingredient in the catalyst and more preferably in the range of about 1.5 to 9 mass-%. Because the fluidized catalyst being recirculated to the OTO conversion reactor must be intimately admixed with the vaporous oxygenate containing feedstream for a period of time dictated by the desired WHSV and thereafter the resulting vapor-solid mixture must be quickly separated in order to provide a stream of deactivated catalyst that at least in part can be charged to the regeneration zone thereby completing the catalyst circulation loop. In order to achieve proper fluidization of the ELAPO catalyst system used in the OTO conversion zone it is necessary to provide the catalyst particles in a particle size distribution in the range of about 1 to 150 microns with the average particle size usually set in the range of about 20 to 100 microns and preferably in the range of about 65 to 85 microns. Due to the opportunities that the catalyst particles have for interacting with each other and the walls of the OTO reactor, its associated regenerator and transport lines the particle size distribution over time will degrade with the generation of a significant amount of catalyst fines due to the abrasive environment experienced in the internal or external catalyst circulation loops. Best practice with respect to OTO reactor configuration is a fluidized bed catalyst system with a fast-fluidized reactor system being particularly preferred. A good example of a preferred fast-fluidized OTO reactor system is shown in U.S. Pat. No. 6,166,282 (the teachings of this '282 patent are specifically incorporated herein by reference). These teachings provide additional details such as the preferred superficial vapor velocity for proper operation of the OTO conversion zone. It is particularly to be noted that the '282 patent incorporates within reactor vessel 10 shown in its drawing three stages of vapor-solid catalyst separation. Although in some cases covered by the instant invention at least one of these stages can be located in a separate surge vessel. The first stage is shown at the top of riser zone 26 wherein the mixture of ELAPO catalyst particles and OTO reaction product stream is discharged through distributor arms 24 into a separation vessel 22 which provides a cyclonic separation action due to the tangential discharge of this mixture of reaction products and catalyst particles. The second stage of vapor-solid separation illustrated in the drawing of this '282 patent is the first cyclone 20 wherein a mixture of fluidized catalyst particles and reaction products is shown as being separated into an overflow vapor stream and a down flowing catalyst particle stream. The third stage of the separation is shown in the drawing of the '282 patent by the operation of closed-couple cyclone separating means 21 which receives as input the overflow stream from the cyclone separating means 20 and produces a second overflow stream which is shown as vented into the overhead plenum of the OTO reaction zone exiting the OTO reaction zone as effluent stream 48. Despite this three stage separation operation provided by the preferred fast-fluidized reactor zone illustrated in the '282 patent the resulting vaporous product effluent stream withdrawn from OTO reactor zone 10 via line 48 still contains significant quantities of the OTO conversion catalyst. Depending on the exact fluidization conditions that are utilized in an OTO reaction zone of the type shown in the '282 patent the product effluent stream withdrawn therefrom can contain catalyst particles in an amount corresponding to 0.01 to 0.1 mass-% with a more typical value being about 0.015 to about 0.05 mass-% of this product effluent stream. Although these quantities of effluent-contaminating catalyst particles appear to be quite small, they represent over time a significant loss of the relatively expensive ELAPO catalyst system (relatively expensive is meant to be relative to the zeolitic catalyst systems such as ZSM-5 of the prior art) and the presence of these contaminating catalyst particles in the product effluent stream give rise to a substantial need for a method for separating and recovery of the catalytic value of these effluent contaminating catalyst particles.

The present invention will be further described in reference to an MTO embodiment using a preferred SAPO-34 catalyst system wherein it has been established to have great utility. The application of the present invention to other oxygenates and to other types of ELAPO catalysts included within its scope is readily within the competence of someone of ordinary skill in the chemical engineering art.

The starting point for the present invention in an MTO embodiment is a MTO conversion step which utilizes methanol as the principal source of the oxygenate reactant. As explained hereinbefore, there are essentially two different approaches to the catalytic conversion of methanol to light olefins. The principal distinction between these two approaches is based on the type of molecular sieve which is used as the active ingredient in the MTO catalyst system and we much prefer the non-zeolitic route to MTO conversion. The details associated with this non-zeolitic or ELAPO route to MTO conversion are summarized in U.S. Pat. No. 5,095,163, U.S. Pat. No. 5,126,308 and U.S. Pat. No. 5,191,141. As indicated above, the preferred ELAPO molecular sieve is a silicoaluminophosphate SAPO system, which has been established as occurring in numerous specific crystal structures. The most preferred SAPO structure for MTO conversion is a SAPO-34 structure. The SAPO-34 molecular sieve can be used alone or may be mixed with a binder and/or filler and formed into shapes such as extrudates, pills, spheres, and the like. A preferred method of forming is to spray dry an aqueous slurry of SAPO-34 powder and filler and/or binder. Any of the inorganic oxides well known in the art may be used as a binder and/or filler such as alumina, silica, alumina-phosphate, silica-alumina, and/or one of the various silica-rich clays such as a kaolin clay that are well known to those of ordinary skill in the art. When a binder and/or filler is used in formulating the SAPO-34 catalyst system, SAPO-34 will usually be present in an amount of about 5 to 90 mass-% of the finished catalyst and preferably about 5 to 60 mass-% thereof. It is to be understood that the active ingredient is the SAPO-34 molecular sieve and the binder and/or filler is a porous material that is used to provide structural integrity to the catalyst particles. A SAPO-34 catalyst system is ordinarily used in an MTO embodiment in a particle size suitable for a fluidized reactor system—typically an average particle size of 65 to 85 microns.

The fluidized MTO reaction zone using a SAPO-34 catalyst is operated at conditions, which include a temperature of about 350° to 600° C. (662° to 1112° F.) with the preferred range being about 450° to 550° C. (842° to 1022° F.). The pressure used in the MTO conversion step is typically in the range of about 138 to 1000 kPa (20 to 145 psia) and preferably from about 170 to 345 kPa (24.7 to 50 psia). The contact time of the reactants with the catalyst is ordinarily measured in terms of a WHSV calculated on the basis of a mass hourly flow rate of the sum of the mass of the methanol reactant passed to the MTO conversion zone plus any other oxygenate reactants present in the feed or recycle streams and any hydrocarbon materials present therein divided by the mass of the SAPO-34 molecular sieve present in the MTO conversion zone. WHSV for use in the MTO conversion zone associated with the present invention can range from 0.1 to 100 $hr^{-1}$, with the best results obtained in the range of about 0.5 to 20 $hr^{-1}$. Since the MTO conversion reaction is strongly exothermic, a significant temperature increase will occur across the MTO reaction zone ordinarily of the magnitude of about 100° to 400° C. (180° to 720° F.). In a fluidized MTO reactor system, an external catalyst circulation rate between the reactor and the regenerator will be set at a minimum level desired to hold average coke on the total circulating inventory of the preferred SAPO-34 catalyst entering the MTO conversion zone in a range of about 1 to 20 mass-% of the active SAPO-34 ingredient in the catalyst and, more preferably, in the range of about 1.5 to 9 mass-%. It is to be recognized that a substantial internal or external catalyst circulation rate may be used around the MTO conversion zone as is shown in U.S. Pat. No. 6,166,282 for purposes of maintaining WHSV, catalyst cooling and/or catalyst mixing.

The regeneration step associated with the MTO conversion step as explained previously will ordinarily use one of the established oxidative techniques for removing the necessary amount of coke from the catalyst prior to recirculation to the conversion zone. The primary factor that will establish the circulation rate between the conversion zone and the regeneration zone is the equilibrium value of coke on catalyst that it is desired to maintain in order to obtain the desired conversion level. SAPO-34 based catalyst systems run quite successfully at conversion levels of 95% or higher and result in a coke made of about 0.6 to 10.4 mass-% of methanol equivalent and more typically 2 to 5 mass-% of methanol equivalent. Knowing the coking rate, one of ordinary skill in the art can then establish a circulation rate to the regenerator based on burning coke at a rate which holds the overall average coke level on the total circulating catalyst inventory used in the MTO conversion zone in the desired range specified hereinbefore. In comparison with traditional hydrocarbon FCC operation, the circulation rate for an MTO fluidized conversion zone will be quite low since the hot regenerated catalyst is not needed to supply heat to the MTO reaction zone.

The methanol feedstock that is charged to the MTO conversion step can ordinarily be used with a diluent as is taught in the prior art acknowledged and incorporated above; however, best practice is not to use a diluent other than autogenously produced steam. The use of a diluent is beneficial in the sense of controlling the partial pressure of the methanol reactant but is disadvantageous in the sense of increasing the volume of the reaction zone and providing additional material that has to be separated from the products in the product recovery section of the process. When a diluent is present in the MTO conversion step, it is preferably steam that is derived from the water that is an inevitable contaminant of the methanol feed stream as well as of the recycle oxygenate streams. Since in many cases it is desired to charge a crude methanol feed stream containing up to about 20 wt-% water, there may in fact be substantial diluent that is brought into the system with the feed stream. In most cases however, it is preferred to run with a methanol feed stream that is 95 to 99.9 mass-% methanol. It is to be recognized that substantial amounts of a steam diluent will be autogenously generated in the first portion of the MTO conversion zone due to the fact that the kinetics of the reaction occurring in the MTO reaction zone are such that the initial formation of DME is extremely fast and results in the formation of one mol of a steam diluent for every 2 mols of methanol that react to produce DME.

DETAILED DESCRIPTION OF THE DRAWING

The following description of the present process is made with reference to the attached drawing. In the interest of simplifying the description of the invention in order to facilitate understanding, the drawing does not contain representations of heaters, heat exchangers, coolers, valves, control means and other conventional items that are well known to those of ordinary skill in the chemical engineering art except where their presence is essential to understanding the present invention.

The attached FIGURE shows the interconnections and interactions between the six zones that form a preferred embodiment of the instant invention. The first zone involved is MTO conversion zone 1 which is shown as being charged via line 7 with a methanol-containing feedstream which preferably enters zone 1 in the form of a substantially vaporous stream. Zone 1 is also shown as being charged with a stream of fluidizable SAPO-34-containing catalyst particles which enter the zone via line 21. Fresh catalyst is typically added to line 21 via an interconnecting line (not shown) in an amount sufficient to replenish the fluidizable catalyst inventory that circulates in and through zone 1 and to and from associated regeneration zone 4. In this embodiment zone 1 operates in a fast-fluidized mode of operation preferably using the fast-fluidized bed reactor shown in the drawing of U.S. Pat. No. 6,166,282 which reactor design incorporates within it three stages of vapor-solid cyclonic separation means as explained hereinbefore. Zone 1 is operated in accordance with the MTO conversion conditions previously discussed to produce a mixture of deactivated catalyst particles and olefinic reaction products. This mixture travels up the riser section of the reaction zone and goes through a series of three stages of vapor-solid separation operations to produce a stream of deactivated catalyst particles and a conversion zone product effluent stream containing light olefins, unreacted oxygenates, $H_2O$, other reaction products and undesired amounts of contaminating catalyst particles. During the course of the highly exothermic MTO reaction that occurs in zone 1 a layer of carbonaceous material coats the outer surface of the catalyst particles and this layer of carbonaceous deposits acts to deactivate the catalyst particles at least in part to the extent that at least a portion of these catalyst particles must have their activity restored in associated catalyst regeneration zone 4. These carbonaceous deposits are commonly referred to as "coke" and are customarily removed by an oxidation procedure as previously explained. A catalyst stream then circulates between zone 1 and zone 4 via lines 22 and 21. At least a portion of the deactivated catalyst material recovered from the three stage cyclonic separation means are stripped of volatile hydrocarbons in zone 1 and passed via line 22 to regeneration zone 4 wherein at least a significant portion of the carbonaceous deposits are oxidatively removed with resulting production of a stream of regenerated catalyst particles which flow via line 21 back to zone 1 for further use in converting the methanol feedstream entering via line 1. The SAPO-34 catalyst system that is preferably utilized to catalyze the MTO conversion reaction is attrition resistant to a level which is comparable to the best FCC catalyst systems known to those of skill in the art. Despite the use of one or more vapor-solid cyclonic separation means in zone 1 to scrub the catalyst particles from the product effluent stream there is in actual practice still a significant amount of catalyst particles that are present in the product effluent stream. These contaminating catalyst particles present a substantial risk to downstream compression means and therefore must be successfully removed prior to olefinic product recovery in downstream recovery and purification zones. The degree of contamination of the product effluent stream by these catalyst particles corresponds to about 0.01 to 0.1 mass-% of the effluent product stream and therefore represents a substantial source of continuing catalyst loss from the catalyst inventory that circulates in and through the MTO conversion zone 1 and the associated catalyst regeneration zone 4.

In accordance with the present invention the product effluent stream withdrawn from MTO conversion zone 1 via line 8 is passed to a catalyst wet scrubbing step performed in zone 2 wherein it is contacted with a scrubbing fluid in order to remove the contaminating catalyst particles contained therein. Prior to entry into zone 2 the relatively hot product effluent stream withdrawn from zone 1 is preferably cooled via one or more techniques not shown in the attached drawing such as passage through a steam generation vessel (i.e. a boiler) and/or by conventional indirect heat exchange against the methanol feedstream in order to reduce the temperature of this product effluent stream to a level where it can be passed into the wet scrubbing zone 2 without excessive flashing of the scrubbing fluid. The temperature of the product effluent stream when it is withdrawn from zone 1 will be in the range of about 350° to 600° C. and sufficient cooling steps will be applied to this stream during its passage through line 8 to reduce its temperature to a level of about 110° to 300° C. when it enters zone 2. The temperature of the product effluent stream will not of course be reduced below the dew point of this stream in order to prevent precipitation of catalyst particles in line 8 where they can precipitate and form a fouling deposit on the walls of line 8 if this minimum temperature requirement is not observed.

In wet scrubbing zone 2 the catalyst-contaminated effluent product stream entering the bottom of zone 2 via line 8 contacts a descending stream of liquid scrubbing fluid which enters an upper region of zone 2 via line 9 and flows countercurrent to the ascending vapor-solid effluent stream. Suitable means for facilitating vapor-liquid contact in zone 2 may be provided and these include appropriately sized solid packing materials as well as suitably designed trays and/or baffles or a combination thereof which act to promote intimate solid-liquid contact. The scrubbing solution used in zone 2 is preferably aqueous and is preferably pumped around zone 2 in a pump-around loop represented by line 9 in the attached drawing. This scrubbing solution will be substantially cooled by means not shown in line 9 prior to reintroduction in order to facilitate a partial quench of the vaporous effluent product stream entering this zone via line 8. Since water is a substantial by-product of the MTO conversion reaction occurring in zone 1 the scrubbing fluid is preferably aqueous and can be replenished by condensation of at least a portion of the water by-product of the MTO conversion reactions which can occur in zone 2 or in a downstream vessel such as zone 3 depending on conditions maintained in zone 2. As is explained in U.S. Pat. No. 6,403,854 the by-products of the MTO conversion zone can include one or more acidic material such as organic acids which are preferably neutralized at least in part via the addition to the aqueous scrubbing fluid of a suitable alkaline material that is compatible with the SAPO-34 catalyst in amounts sufficient to neutralize at least a substantial portion of these acidic materials in order to prevent corrosion and fouling of the wet scrubbing zone as well as the downstream flow conduits and equipment. This alkaline reagent such as a suitable amine can be added to the scrubbing liquid circulating in line 9 via an alkaline reagent injection line not shown in the attached drawing. Zone 2 is operated at scrubbing conditions effective to produce an overhead vapor stream 10 which is substantially free of particles of the SAPO-34 catalyst system and essentially comprises the olefinic and other hydrocarbon products of the MTO conversion reactions occurring in zone 1 plus all or a substantial portion of the by-product water and any unreacted oxygenates such as methanol and DME that accompany this material. The liquid bottom stream produced in zone 2 comprises a mixture of the contaminating catalyst particles in the scrubbing liquid and it is withdrawn from this zone via line 9 and preferably recycled through pumping means and cooling means, not shown, to reenter the upper region of zone 2. Depending on operating conditions a portion of the water by-product produced in MTO conversion zone 1 as well as a portion of the water soluble products and reactants may be removed from zone 2 along with the contaminating catalyst particles via line 9. As is explained the '854 patent zone 2 not only functions as a catalyst scrubbing zone but also as a first stage quench zone reducing the temperature of the vapor overhead stream withdrawn via line 10 by an incremental amount of about 10 to 200° C. relative to the temperature of the material entering zone 2 via line 8. The circulation rate of scrubbing liquid around and through zone 2 via line 9 is set such that the mass ratio of scrubbing liquid to the mass of entering product effluent stream is about 0.5:1 to 3:1 with the best results obtained at a scrubbing fluid to effluent mass ratio of about 0.8:1 to 1.5:1. It is a preferred practice in the operation of wet scrubbing zone 2 to allow the concentration of catalyst particles withdrawn in the mixture or slurry of these particles with scrubbing fluid contained in line 9 to build to a level such that this circulating catalyst slurry contains about 0.5 to 5 mass-% catalyst particles and preferably about 0.35 to 0.65 mass-% catalyst particles. A drag stream from this circulating scrubbing fluid (or catalyst slurry) is preferably withdrawn via lines 9 and 16 and passed continuously to a catalyst slurry dewatering zone 5 in order to further concentrate this slurry of catalyst particles in scrubbing fluid prior to recirculation to the MTO conversion zone 1 or to regeneration zone 4. In the case where scrubbing zone 2 is operated at conditions that result in the flashing of scrubbing fluid in an amount requiring the addition of water, make-up water can be added to line 9 via line 25 and this water can be obtained from zone 3 via lines 11, 13, 26 and 25 or from zone 5 via lines 17 and 25, or from a combination of these sources.

In accordance with the teaching of the '854 patent the overhead vapor stream recovered from scrubbing zone 2 via line 10 is passed to effluent quench zone 3 wherein this vapor stream is further cooled in order to remove the residual portion of the by-product water not recovered wet scrubbing zone 2 and any scrubbing fluid flashed off in zone 2. Zone 3 is operated in accordance with the teachings of the '854 patent for its second quench zone 46. It is to be noted that there may in fact be one or more intercoolers located in line 10 (not shown) that can be utilized to further lower the temperature of the overhead stream from the wet scrubbing zone 2 and to provide an opportunity for heat integration with various other streams charged to one or more of the involved conversion zones. The quenching fluid that is used in zone 3 is preferably water and it is injected into the upper region of zone 3 and counter currently contacts an ascending vaporous stream which enter the zone via line 10. The quenching conditions maintained in zone 3 are sufficient to further quench the vaporous portion of the product effluent stream which is injected into this zone via line 10 to provide an opportunity to further reduce the water content and unreacted oxygenate content of this stream. Zone 3 is operated at quenching conditions effective to produce an olefin-rich overhead vapor stream containing trace amounts of unreacted oxygenates (primarily methanol and DME) which is passed via line 12 to downstream facilities for further purification and recovery of the light olefins contained therein. The liquid bottom stream from zone 3 is an aqueous quenching stream that is preferably pumped around zone 3 via line 11 through pumping means (not shown) and further cooled via cooling means (not shown) to produce a quenching medium that is at a temperature of about 20° to 75° C. prior to injection into quenching zone 3. In the drawing a water-rich drag stream is shown as being withdrawn from this circulating quenching fluid loop via lines 11 and 13 and at least a portion of this drag stream is charged to the upper region of oxygenate stripping zone 6. In the case where zone 2 operates to consume water, at least a portion of this drag stream can be passed to zone 2 via lines 13, 25, 26 and 9.

Oxygenate stripping zone 6 operates to strip any unreacted oxygenates such as methanol and DME from the aqueous streams charged thereto and to produce a relatively pure water stream which is withdrawn from the bottom of the stripping zone via line 14 and is available for further use in the process if for example it is desired to use an aqueous diluent in the operation of MTO conversion zone 1. Use of the water stream recovered via line 14 for this purpose however is not favored because of the additional load requirement it puts on the wet scrubbing zone 2 and quenching zone 3 associated with the instant invention. That is to say that if substantial amounts aqueous diluent are recirculated to zone 1 both wet scrubbing zone 2 and effluent zone 3 must be expanded to accommodate this additional vapor traffic. Stripping zone 6 is operated at oxygenate stripping conditions effective to produce an overhead vapor stream which exits zone 6 via line 15 and comprises a significant portion of the net unreacted oxygenates recovered from the effluent stream from zone 1 in zones 2 and 3 and it can be recycled via lines 15 and 7 to MTO conversion zone 1 in order to enhance the conversion of oxygenates that occurs in zone 1. All or a portion of this overhead stream 15 may be routed to zone 3 or into line 12, via transfer lines not shown in the drawing, in order to consolidate the unreacted oxygenate recovery and recycle with the downstream purification of the overhead stream in line 12.

The operation of catalyst slurry dewatering zone 5 it is designed to further concentrate the catalyst particles recovered in wet scrubbing zone 2 prior to recycle of these recovered particles to MTO conversion zone 1 or to regeneration zone 4. The use of dewatering zone 5 is an optional feature of the present invention that is preferred since it diminishes the amount of scrubbing fluid that accompanies the recycled stream of catalyst particles. In operation dewatering zone 5 will comprise a set of one or more solid-liquid separating means that operate in series or in parallel or in a combination of series and parallel flow configurations to dewater the catalyst slurry that enters the upper region of zone 5 via lines 9 and 16 suitable liquid-solid separating means for use in this separating step include hydrocyclones, filters, centrifuges, slurry settlers and combinations of one or more of these separating means. For purposes of the present invention, we prefer to use liquid-solid cyclones or hydrocyclones for this application in view of their efficiency and relatively low capital and operating costs but any other suitable liquid-solid separating means can be used for their applications if locally available. Liquid cyclones are well known to those of skill in the chemical engineering art and essentially comprise a top cylindrical section and a lower conical section terminating in an apex opening which is used to withdraw a solid-containing stream 18 which is relatively rich in the entering particles of catalyst. The solid-rich stream withdrawn via lines 18 from the apex of the conical section of as solid-liquid cyclone is also sometimes referred to as the solid-containing underflow stream. The liquid feedstream entering zone 5 via line 16 is pressured by pumping means (not shown) and tangentially injected into the cylindrical portion of the one or more cyclonic separating means contained in zone 5 in order to produce a vortexing effect due to the centrifugal motion induced thereby. The top of this dewatering zone ordinarily contains one or more downward-extending pipes that cuts the vortex in each of these cyclonic separating means and connect to line 17, where a solid-lean liquid stream, typically called an overflow stream which is substantially reduced in catalyst particle content relative to the entering stream is recovered. Zone 5 preferably contains at least one of these liquid-solid cyclones but in some heavy load operations it may be necessary to connect together a series of one or more trains of liquid-solid cyclones of standard size in zone 5 in order to concentrate the catalyst particles in an optimum manner for recycle to MTO conversion zone 1. Similarly it may be necessary to use a parallel arrangement of liquid-solid cyclones of standard size in order to efficiently accommodate the volume of material that can be passed into dewatering zone 5 via line 16. The details associated with the number and arrangement of the liquid-solid cyclones contained in zone 5 to perform a given job are well known to those skilled in the liquid-solid separating art and need not be described further here.

The solid-lean stream from dewatering zone 5 withdrawn via line 17 primarily comprises the aqueous scrubbing liquid used in zone 2 with trace amounts of very fine particles of the SAPO-34 catalyst that contaminated the effluent stream withdrawn from MTO conversion zone 1. As previously explained at least a portion of this overflow stream is preferably passed via lines 17, 25 and 9 to wet scrubbing zone 2 when zone 2 is operated with net water consumption in order to recover and recycle a substantial portion of the aqueous scrubbing liquid contained therein. A drag stream is taken from this overflow stream via line 17 in order to prevent the build-up of any fine particles of the catalyst in the circuit between zones 2 and 5. This drag stream is passed downstream for recovery of any unreacted oxygenates contained therein and for suitable disposal of the very fine particles of catalyst contained therein. The solid-rich stream withdrawn from dewatering zone 5 via line 18 represents a relatively concentrated slurry of SAPO-34 catalyst particles in scrubbing liquid and the catalyst particles will comprise about 5 to 30 mass-% of this underflow stream. The heart of the present invention is the recognition that the catalyst particles that are present in underflow stream 18 contain catalytic SAPO-34 material that can be reused in promoting additional MTO conversion reactions thereby substantially lessening the amount of fresh catalyst that is necessary to add to zone 1 to maintain the inventory of circulating catalyst that passes in and through zones 1 and 4. As shown in the attached drawing this underflow stream can be used to reinject these recovered catalyst particles at a number of different points in the circulating catalyst stream flowing in and around zones 1 and 4. If desired this material can be directly injected into MTO conversion zone via line 18 wherein the water contained in this stream will serve as diluent to the MTO conversion reaction thereby lowering the partial pressure of the oxygenate reactants to some extent. If the recycled catalyst stream is injected into the MTO conversion zone it is preferred to inject it into the stripping zone which is part of the disengagement zone that sits atop the riser reaction zone shown in the preferred fast-fluidized apparatus of U.S. Pat. No. 6,166,282. A second option with respect to the injection of this recycled catalyst stream is to pass it directly into the regeneration zone via lines 18 and 19 wherein it can be stripped of its protective layer of carbonaceous material via a conventional oxidation regeneration procedure with the resulting regenerated particles passed via line 21 back to MTO conversion zone 1 where they can participate in further promoting catalytic MTO reactions. A third, less preferred choice, is to inject these recovered catalyst particles directly into the return standpipe which is at a relatively high temperature and contains regenerated particles. This is accomplished by passing this stream via lines 18 and 20 into line 21 wherein they are returned to the MTO conversion zone. Suitable valves not shown in the attached drawing are used to block off the appropriate lines to accomplish the flows as outlined above through these various alternative flow conduits. In this last alternative where the recovered catalyst stream is passed directly into the standpipe containing regenerated catalyst contained in line 21 it is of course to be noted that the deactivating coat of carbonaceous deposits contained on these materials will prevent these particles from contributing any substantial amount of catalytic activity to the MTO conversion zone until they have been recirculated to the regenerator in the ordinary course of the operations of zones 1 and 4.

Catalyst regeneration zone 4 is shown in the attached drawing as being charged with oxygen-containing regeneration gas entering this zone via line 24 and operating to produce a flue-gas stream which is shown as exiting regeneration zone 4 via line 23. In accordance with the normal practice for carbonaceous deposit removal from SAPO-34 types of catalyst, an oxidation reaction is performed in regeneration zone 4 utilizing sufficient oxygen to establish combustion in regeneration zone 4 thereby converting the deactivating carbonaceous deposits into water and $CO_2$ which are eliminated from the process via flue-gas line 23. It is to be understood that flue-gas line 23 will also typically contain an amount of very fine catalyst particles that are removed from this flue-gas stream prior to its release into the atmosphere utilizing various separation techniques well known to those of skill in the art. Flue-gas line 23 will then constitute the principal means for elimination from the circulating catalyst stream utilized in zones 1 and 4 of very fine particles that are produced by attrition and fragmentation of the SAPO-34 catalyst system as it undergoes the stresses associated with the turbulence induced by flow through these zones. By means of the present invention approximately 75 to 99 plus mass-% of the catalyst particles exiting MTO conversion zone 1 via line 8 are recovered and recycled to MTO conversion zone 1 for further use therein. This stands in sharp contrast to the prior art schemes that utilize the wet scrubbing zone but discarded the resulting recovered catalyst particles into a waste stream apparently not recognizing that these catalyst particles retain substantial activity for promoting the desired MTO conversion reaction.

The following examples are presented in order to facilitate an understanding of the present invention and to prove that the contaminating catalyst particles recovered from the product effluent stream from an MTO conversion zone retained substantial catalytic activity for promoting the MTO conversion reactions. These examples are however presented for purposes of illustration rather then limitation.

EXAMPLE 1

In order to demonstrate the protective effect of coke content on the activity-stability characteristics of an MTO catalyst-containing SAPO-34 when it is immersed in an aqueous scrubbing solution in accordance with the wet scrubbing step of the present invention, an experiment was conducted in which a sample of a typical non-zeolitic MTO catalyst was subjected to an aqueous immersion step with and without the protective benefit of a layer of coke deposits. In addition, a second control catalyst was tested in order to benchmark the activity-stability performance of a coke-free catalyst that had not been subjected to an aqueous immersion step.

The composition of the typical non-zeolitic MTO catalyst was 40 mass-% SAPO-34, 40-mass-%, kaolin clay and 20 wt-% silica-alumina binder. The SAPO-34 material was synthesized in accordance with the methodology specified in U.S. Pat. No. 5,191,141. This catalyst in a coke-free form had a piece density of 1.075 g/cc and an average particle size of about 75 microns (i.e. micrometers). This catalyst had been used to catalyze MTO conversion reactions in a fluidized reaction zone until it had accumulated an equilibrium level of coke which corresponded to 6 mass-% carbonaceous deposits. The catalyst was then stripped of volatile material and then divided into 3 portions. The first portion, hereinafter referred to as Catalyst A, was a sample of the coke-containing catalyst as recovered from the fluidized pilot plant unit. Three separate 50 gram samples of Catalyst A were then taken and subjected to a sequence of a water immersion step followed by a regeneration step conducted under the conditions specified below to prepare a coke-free catalyst for testing in the activity-stability test below. The second portion of the starting catalyst, hereinafter referred to as Catalyst B was subjected to the regeneration step described below to prepare a coke-free material which was then subjected to the aqueous immersion step described below. The third portion, hereinafter referred to as Catalyst C, was subjected to the regeneration step described below in order to produce a coke-free catalyst which was tested directly in the activity-stability test described below without any exposure to the aqueous immersion step in order to provide a fully regenerated control catalyst for the experiment. Catalysts B and C are both control catalysts.

The water immersion step in this experiment involves subjecting a 50 gram sample of the particular catalyst to immersion in 100 to 500 grams of distilled water at a temperature and a holding time which is specified in Table 1. In all cases sufficient pressure was maintained on the mixture of catalyst and water to maintain a liquid-phase condition for the period of immersion.

The regeneration step used in the experiment involved subjecting the coke-containing catalyst sample to a drying step involving exposure to a dry gas stream for 3 to 12 hours at a temperature of about 100° to 120° C. The resulting dried catalyst sample was then subjected to a treatment with an air stream at coke combustion conditions which included a temperature of 650° C. for a coke combustion period of 5 hours which in all cases was sufficient to remove substantially all of the coke deposits.

The resulting regenerated catalysts were then subjected to an MTO conversion breakthrough test designed to measure catalyst activity-stability which involved loading 10 grams of the regenerated catalyst sample into a fixed bed pilot plant reactor and charging thereto a vaporized feed comprising 80 mass-% methanol and 20 mass-% distilled water (i.e. steam) present as a diluent. During the test, the reactor was maintained at a pressure of 138 kPa (5 psig), a WHSV of 2.5 hr$^{-1}$ (based on grams of methanol charged per hour/grams of SAPO-34 present in the reactor) and a reactor inlet temperature of 435° C. (815° F.) measured near the point of introduction of vaporized feed. The test in all cases was conducted until one mass-% of unreacted oxygenates (i.e. methanol and/or dimethylether) was detected in the product effluent stream at which point the conversion level in the reaction zone had dropped to 99 mass-% of the methanol charged. This point of oxygenate breakthrough into the effluent stream was measured in terms of hours on stream (HOS) and the number for each of the catalyst samples is reported in Table 1. In this breakthrough test the magnitude of the HOS number is a good reproducible measure of the activity-stability of the particular catalyst sample in an MTO conversion application.

The results of a series of experiments assessing the effect of an immersion step on the activity-stability of the SAPO-34 catalyst samples is set forth in Table 1.

TABLE 1

Effect of Aqueous Immersion On The Activity-Stability of SAPO-34 MTO Catalyst

| RUN NO. | CATALYST | IMMERSION STEP | REGENERATION STEP | IMMERSION T, ° C. and t, hr | HOS |
|---|---|---|---|---|---|
| 1 | A | Yes | Yes | 40, 48 | 3.4 |
| 2 | A | Yes | Yes | 90, 3 | 3.3 |
| 3 | A | Yes | Yes | 110, 3 | 3.4 |
| 4 | B | Yes | Yes | 40, 48* | 3.1 |
| 5 | C | No | Yes | None | 3.4 |

*Catalyst B was regenerated prior to the immersion step so it was coke-free in this step.

The activity-stability test results presented in Table 1 demonstrate the expected adverse effect of an aqueous immersion step on the performance of an unprotected MTO catalyst. Evidence to support this is found by comparing the HOS results for run 5 (i.e. performed with Catalyst C that had not been exposed to the aqueous immersion step) with the results for run 4 (performed with Catalyst B which had no protective layer of coke deposits when subjected to aqueous immersion) where a decrease of 8.8 mass-% in HOS was recorded. This HOS measure is a sensitive indicator of relative activity-stability and a decrease of 8.8% corresponds to a substantive drop in activity-stability.

Quite surprisingly, runs 1, 2 and 3 dramatically demonstrate that the aqueous immersion step does not damage the performance of the three samples of Catalyst A that were tested since all of these runs Catalyst A had a protective layer of coke deposits at a level of 6 mass-% when it was subjected to the aqueous immersion step. The HOS results for the three samples of Catalyst A clearly show that their activity-stability was equal to or comparable to the activity-stability measured in run 5 for Catalyst C which is the control catalyst which was not exposed to an aqueous immersion step. Data presented in Table 1 for runs 1, 2 and 3 thus provide convincing evidence that the harmful effect of aqueous immersion can be avoided with a SAPO-34 MTO catalyst system if the aqueous immersion is conducted with a catalyst that contains a protective coat of coke deposits.

EXAMPLE 2

In order to study the effect of thermal shock on a wet scrubbing MTO catalyst that had been withdrawn from an aqueous immersion step, an experiment was conducted wherein two 50 gram portions of Catalyst A were exposed to an aqueous immersion step conducted at a temperature of 40° C. for a period of 48 hours as explained above. The resulting wet scrubbing catalyst in the case of run 6 was subjected to a thermal shock step which essentially involved quickly placing the wet scrubbing catalyst that was withdrawn from the immersion step in a box oven that was maintained at 650° C. and an ambient pressure at a period of 5 minutes. These conditions were chosen to simulate a worst case scenario when the catalyst that was withdrawn from the wet scrubbing step is immediately exposed to a high temperature condition in the MTO conversion step or the regeneration step of the present invention. The temperature differential was set at a level of 610° C. in order to accomplish this objective. In run 6 the catalyst was subjected to the immersion step followed by the thermal shock step followed by the regeneration step that was described in Example 1. In run 7 the sample of Catalyst A was not subjected to the thermal shock step but was in fact subjected to the wet scrubbing immersion step followed by the regeneration step. Both of these samples of catalyst were then subjected to the MTO conversion breakthrough test designed to measure activity-stability which was described above in Example 1.

The results of the experiment are presented in Table 2 wherein the run with the thermal shock is contrasted with a run in which the catalyst was not thermally shocked. As can be seen from Table 2 the HOS numbers for the two samples of Catalyst A are identical and thus there was no effect of the thermal shock step on the activity-stability of the SAPO-34-containing MTO catalyst.

TABLE 2

Effect of Thermal Shock On A Wet Scrubbing MTO Catalyst

| RUN NO. | CATALYST | IMMERSION STEP | THERMAL SHOCK STEP | IMMERSION T, ° C. and t, hr | HOS |
|---|---|---|---|---|---|
| 6 | A | Yes | Yes | 40, 48 | 3.4 |
| 7 | A | Yes | No | 40, 48 | 3.4 |

Both of the catalysts that were tested for purposes of preparing Table 2 were also sent out for a scanning electron microscope check to ascertain whether or not there had been any significant change in their morphology. The results of this SEM analysis showed that approximately 1 to 2% of the catalyst particles in the sample that had been exposed to thermal shock step were fractured or cracked by this procedure. This low rate of fractionating of the SAPO-34 catalyst particles was viewed as a result extremely favorable to the practice of the present invention.

We claim as our invention:

1. A process for the catalytic conversion of a feedstream containing an oxygenate to light olefins using a fluidized conversion zone and a relatively expensive fluidized catalyst containing an ELAPO molecular sieve with recovery and recycle of contaminating catalyst particles from the product effluent stream withdrawn from the conversion zone, which process comprises the steps of:
   a) contacting the feedstream with the fluidized catalyst in the fluidized conversion zone at conversion conditions effective to form a mixture of deactivated catalyst particles and olefinic reaction products;
   b) separating at least a portion of the deactivated catalyst particles from the resulting mixture in a vapor-solid separating zone containing at least one vapor-solid cyclonic separating means to form a stream of deactivated catalyst particles and a conversion zone product effluent stream containing light olefins, unreacted oxygenates, $H_2O$, other reaction products and undesired amounts of contaminating catalyst particles;

c) passing the conversion zone product effluent stream to a wet scrubbing zone and therein contacting the effluent stream with a scrubbing liquid under scrubbing conditions effective to form a substantially catalyst-free overhead stream containing light olefins and a liquid bottom stream containing a mixture of the contaminating catalyst particles and the scrubbing liquid;

d) passing at least a portion of the stream of the deactivated catalyst particles formed in step (b) to a regeneration zone and therein contacting the deactivated catalyst particles with an oxidizing gas stream under oxidizing conditions effective to form a stream of regenerated catalyst particles;

e) recycling at least a portion of the liquid bottom stream produced in step (c) to step (a); and f) passing at least a portion of the stream of regenerated catalyst particles from step (d) to step (a).

2. The process as defined in claim 1 wherein the oxygenate is an oxygen-substituted aliphatic material containing 1 to 4 carbon atoms.

3. The process as defined in claim 2 wherein the oxygen-substituted aliphatic material is an alcohol, an ether, an aldehyde, an ketone or mixtures thereof.

4. The process as defined in claim 1 wherein the oxygenate is methanol or dimethylether or a mixture thereof.

5. The process as defined in claim 1 wherein the ELAPO molecular sieve is a SAPO molecular sieve.

6. The process as defined in claim 5 wherein the SAPO molecular sieve is SAPO-34 or SAPO-17 or mixture thereof.

7. The process as defined in claim 1 wherein the fluidized conversion zone is a fast-fluidized bed reactor system.

8. The process as defined in claim 1 wherein at least a portion of the liquid bottom stream from the wet scrubbing zone is recirculated to the scrubbing zone in order to allow the concentration of the contaminating catalyst particles to increase in the bottom stream.

9. The process as defined in claim 1 wherein at least a portion of the liquid bottom stream recovered from the wet scrubbing zone is passed to a liquid-solid separating zone containing one or more liquid-solid separating means operated under separating conditions effective to produce an solid-rich stream containing a relatively rich slurry of contaminating catalyst in the scrubbing liquid and a relatively solid-lean stream containing scrubbing liquid wherein at least a portion of the underflow stream is recycled to step (a).

10. The process as defined in claim 1 wherein the scrubbing liquid used in step (c) is water.

11. The process as defined in claim 1 wherein the scrubbing liquid used in step (c) is water containing an alkaline reagent compatible with the catalyst in an amount sufficient to neutralize a significant portion of any acidic by-products of the oxygenate conversion reaction.

12. The process as defined in claim 1 wherein the contaminating catalyst particles contain deactivating coke deposits in an amount sufficient to prevent any substantial damage to their catalytic activity when they are exposed to the hydrothermal shock of step (c) or the thermal shock of step (d).

13. The process as defined in claim 1 wherein the conversion zone product effluent stream is substantially cooled between steps (b) and (c).

14. The process as defined in claim 1 wherein the conversion zone product effluent stream is at a temperature of about 350° to about 600° C. upon exit from step (b) and step (c) is operated to produce a liquid bottom stream having a temperature of about 100° to about 135° C.

15. A process for the catalytic conversion of a feedstream containing methanol to light olefins using a fluidized conversion zone and a relatively expensive fluidized catalyst containing a SAPO molecular sieve with recovery and recycle of contaminating catalyst particles from the product effluent stream withdrawn from the conversion zone, which process comprises the steps of:

a) contacting the feedstream with the fluidized catalyst in the fluidized MTO conversion zone at conversion conditions effective to form a mixture of deactivated catalyst particles and olefinic reaction products; b) separating at least a portion of the deactivated catalyst particles from the resulting mixture in a vapor-solid separating zone containing at least one vapor-solid cyclonic separating means to form a stream of deactivated catalyst particles and an MTO conversion zone product effluent stream containing light olefins, unreacted methanol, $H_2O$, other reaction products including DME and undesired amounts of contaminating SAPO-containing catalyst particles;

c) passing the MTO conversion zone product effluent stream to a wet scrubbing zone and therein contacting the effluent stream with a scrubbing liquid under scrubbing conditions effective to form a substantially catalyst-free overhead stream containing light olefins and a liquid bottom stream containing a mixture of the contaminating catalyst particles and the scrubbing liquid;

d) passing at least a portion of the steam of the deactivated catalyst particles formed in step (b) to a regeneration zone and therein contacting the deactivated catalyst particles with an oxidizing gas stream under oxidizing conditions effective to form a stream of regenerated catalyst particles;

e) recycling at least a portion of the bottom stream produced in step (c) to step (a); and f) passing at least a portion of the stream of regenerated catalyst particles from step (d) to step (a).

16. The process as defined in claim 15 wherein the SAPO molecular sieve is SAPO-34 or SAPO-17 or a mixture thereof.

17. The process as defined in claim 15 wherein the fluidized MTO conversion zone is a fast-fluidized bed reactor system.

18. The process as defined in claim 15 wherein at least a portion of the liquid bottom stream from the wet scrubbing zone is recirculated to the scrubbing zone in order to allow the concentration of the contaminating catalyst particles to increase in the bottom stream.

19. The process as defined in claim 15 wherein at least a portion of the liquid bottom steam recovered from the wet scrubbing zone is passed to a liquid-solid separating zone containing one or more liquid-solid separating means operated under separating conditions effective to produce a solid-rich underflow steam containing a relatively rich slurry of contaminating catalyst in the scrubbing liquid and a relatively solid-lean stream containing scrubbing liquid wherein at least a portion of the solid-rich stream is recycled to step (a) or to step (d).

20. The process as defined in claim 15 wherein the scrubbing liquid used in step (c) is water.

21. The process as defined in claim 15 wherein the contaminating SAPO-containing catalyst particles contain deactivating coke deposits in an amount sufficient to prevent any substantial damage to their catalytic activity when they are exposed to the hydrothermal shock of step (c) or the thermal shock of step (d).

22. The process as defined in claim 15 wherein the MTO conversion zone product effluent stream is substantially cooled between steps (b) and (c).

* * * * *